United States Patent [19]

Toukhy et al.

[11] Patent Number: 5,220,073

[45] Date of Patent: Jun. 15, 1993

[54] SELECTED TRIHYDROXYBENZOPHENONE COMPOUNDS

[75] Inventors: Medhat A. Toukhy, Barrington; Alfred T. Jeffries, III, Providence, both of R.I.

[73] Assignee: OCG Microelectronic Materials, Inc., Cheshire, Conn.

[21] Appl. No.: 979,849

[22] Filed: Nov. 23, 1992

Related U.S. Application Data

[62] Division of Ser. No. 661,928, Feb. 28, 1991, which is a division of Ser. No. 429,298, Oct. 30, 1989, Pat. No. 5,019,478.

[51] Int. Cl.$^5$ .............................. C07C 49/245
[52] U.S. Cl. .................................... 568/333
[58] Field of Search ......................... 568/333

[56] References Cited

U.S. PATENT DOCUMENTS

| | | | |
|---|---|---|---|
| 2,686,123 | 8/1954 | Campbell et al. | 568/333 |
| 2,900,361 | 8/1959 | Havens | 568/333 |
| 3,395,184 | 7/1968 | Dressler et al. | 568/333 |
| 4,288,631 | 9/1981 | Ching | 568/333 |

FOREIGN PATENT DOCUMENTS 49-48317  12/1974  Japan .................... 568/333

OTHER PUBLICATIONS

Toukhy et al, Chem. Abst., vol. 112, #27934a (1990).

*Primary Examiner*—James H. Reamer
*Attorney, Agent, or Firm*—William A. Simons

[57] ABSTRACT

A trihydroxybenzophenone compound of the formula (I):

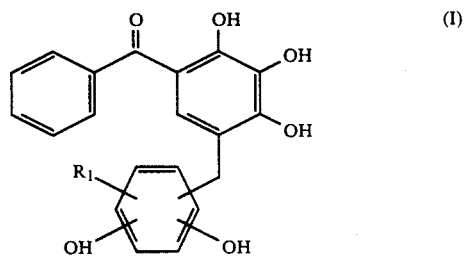

wherein $R_1$ is selected from the group consisting of hydroxyl group, halide group, a lower alkyl group having 1 to 4 carbon atoms, and a lower alkoxy group having 1 to 4 carbon atoms.

5 Claims, No Drawings

SELECTED TRIHYDROXYBENZOPHENONE COMPOUNDS

This application is a division of application Ser. No. 07/661,928 filed Feb. 28, 1991, which is a division of application Ser. No. 07/429,298 filed Oct. 30, 1989 now U.S. Pat. No. 5,019,478 issued on May 28, 1991.

The present invention relates to selected trihydroxybenzophenone compounds useful as backbones for certain photoactive compounds. Further, the present invention relates to such photoactive compounds formed by the esterification of these trihydroxybenzophenone compounds with sulfonyl halides of o-naphthoquinone diazides. Still further, the present invention also relates to radiation sensitive mixtures (e.g. those particularly useful as positive-working photoresists) containing the combination of these photoactive compounds with alkali-soluble binder resins dissolved in a solvent. And furthermore, the present invention also relates to substrates coated with these radiation sensitive mixtures as well as the process of coating, imaging and developing these radiation sensitive mixtures on these substrates.

Photoresist compositions are used in microlithographic processes for making miniaturized electronic components such as in the fabrication of integrated circuits and printed wiring board circuitry. In these processes, a thin coating or film of a photoresist composition is generally first applied to a substrate material, such as silicon wafers used for making integrated circuits or aluminum or copper plates of printed wiring boards. The coated substrate is then baked to evaporate any solvent in the photoresist composition and to fix the coating onto the substrate. The baked coated surface of the substrate is next subjected to an image-wise exposure of radiation. This radiation exposure causes a chemical transformation in the exposed areas of the coated surface. Visible light, ultraviolet (UV) light, electron beam, ion beam and X-ray radiant energy are radiation types commonly used todaY in microlithographic processes.

After this image-wise exposure, the coated substrate is treated with a developer solution to dissolve and remove either the radiation-exposed or the unexposed areas of the coated surface of the substrate. In some processes, it is desirable to bake the imaged resist coating before this developing step. This intermediate step is sometimes called post-exposure bake or PEB.

There are two types of photoresist compositions —negative-working and positive-working. When negative-working photoresist compositions are exposed image-wise to radiation, the areas of the resist composition exposed to the radiation become less soluble to a developer solution (e.g. a cross-linking reaction occurs) while the unexposed areas of the photoresist coating remain relatively soluble to a developing solution. Thus. treatment of an exposed negative-working resist with a developer solution causes removal of the non-exposed areas of the resist coating and the creation of a negative image in the photoresist coating, and thereby uncovering a desired portion of the underlying substrate surface on which the photoresist composition was deposited. On the other hand, when positive-working photoresist compositions are exposed image-wise to radiation, those areas of the resist composition exposed to the radiation become more soluble to the developer solution (e.g. the Wolff rearrangement reaction of the photactive compound occurs) while those areas not exposed remain relatively insoluble to the developer solution. Thus, treatment of an exposed p ositive-working resist with the developer solution causes removal of the exposed areas of the resist coating and the creation of a positive image in the photoresist coating. Again, a desired portion of the underlying substrate surface is uncovered.

Positive-working photoresist compositions are currently favored over negative-working resists because the former generally have better resolution capabilities and pattern transfer characteristics.

After this development operation, the now partially unprotected substrate may be treated with a substrate-etchant solution or plasma gases and the like. This etchant solution or plasma gases etch the portion of the substrate where the photoresist coating was removed during development. The areas of the substrate are protected where the photoresist coating still remains and, thus, an etched pattern is created in the substrate material which corresponds to the photomask used for the image-wise exposure of the radiation. Later, the remaining areas of the photoresist coating may be removed during a stripping operation, leaving a clean etched substrate surface. In some instances, it is desirable to heat treat the remaining resist layer after the development step and before the etching step to increase its adhesion to the underlying substrate and its resistance to etching solutions.

End users of photoresists are demanding photoresist formulations which possess better lithographic properties for the fabrication of smaller microelectronic circuits. The lithographic properties which are critical to these end-users include the following: (1) good resolution capabilities in both the micron and submicron ranges without incomplete development in the exposed areas (i.e. scumming); (2) higher thermal image deformation temperatures (e.g. above 120° C.) (3) relatively fast photospeeds; (4) good adhesion to substrate; (5) good developer dissolution rates; (6) good process latitute; (7) near to absolute vertical profiles (or good contrast) between exposed and unexposed photoresist areas after development; (8) good resistance to etching solutions and plasma etching techniques; (9) reduced tendency to form insoluble particulates and (10) mask linearity.

Generally, in the past efforts to improve one of these lithographic properties have caused significant decreases in one or more of the other lithographic properties of the photoresist. Accordingly, there is a need for improved photoresist formulations which possess all of these desired properties. The present invention is believed to be an answer to that need.

Accordingly, the present invention is directed to selected trihydroxybenzophenone compounds of formula (I):

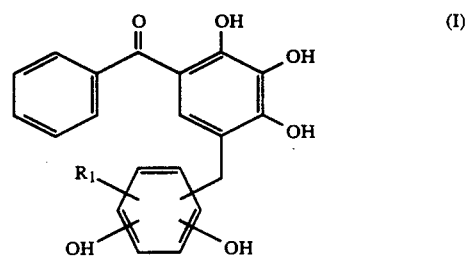

wherein $R_1$ is selected from the group consisting of hydroxyl group, a halogen group (i.e., Cl, Br, I, and F), a lower alkyl group having from 1 to 4 carbon atoms, and a lower alkoxy group having 1 to 4 carbon atoms.

Moreover, the present invention is directed to photoactive o-naphthoquinone diazide sulfonyl moieties of said trihydroxybenzophenone compounds having formula (V):

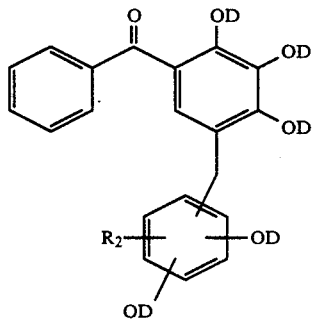
(V)

wherein $R_2$ is selected from the group consisting of an OD group, a halogen (i.e., Cl, Br, I, and F) group, a lower alkyl group having 1 to 4 carbon atoms and a lower alkoxy group having 1 to 4 carbon atoms; and wherein each D is an o-naphthoquinone diazide sulfonyl moiety or a hydrogen atom, with the proviso at least four D's are o-naphthoquinone diazide sulfonyl moieties.

Moreover, the present invention is directed to a radiation sensitive mixture useful as a positive photoresist comprising an admixture of at least one photoactive o-naphthoquinone diazide compound of formula (II) above and an alkali-soluble binder resin; the amount of said photoactive o-naphthoquinone diazide compound or compounds being about 5% to about 30% by weight and the amount of said binder resin being about 70% to 95% by weight, based on the total solids content of said radiation sensitive mixture.

Still further, the present invention also encompasses the process of coating substrates with these radiation sensitive mixtures and then exposing and developing these coated substrates.

Also further, the present invention encompasses said coated substrates (both before and after imaging) as novel articles of manufacture.

The selected trihydroxybenzophenone compounds of formula (I) are made by reactin9 2,3,4-trihydroxy-5-methylolbenzophenone with a selected dihydroxy- or trihydroxy-benzene compound under acidic pH conditions.

The 2,3,4-trihydroxy-5-methylolbenzophenone precursor may be made from 2,3,4-trihydroxybenzophenone and formaldehyde. Its synthesis is disclosed in Example 1 below and in U.S. patent application Ser. No. 07/200,676 which was filed on May 31, 1988 with Medhat Toukhy as the named inventor.

Preferred dihydroxy- or trihydroxybenzene compounds include 1,3,5-trihydroxybenzene, 4-chlororesorcinol, and 3-methoxy-5-hydroxyphenol.

In making this class of trihydroxybenzophenone compounds of formula (I), the precursors are preferably present in the reaction vessel in a mole ratio of 2,3,4-trihydroxy-5-methylolbenzophenone to the di- or trihydroxybenzene compound from about 5:1 to about 20:1, preferably from about 5:1 to about 15:1. The preferred reaction temperature is about 60°–100° C. at atmospheric pressure. Preferably, this reaction occurs in the presence of a solvent and an acid catalyst. The preferred solvent is water. Suitable acid catalysts include those commonly employed in acid condensation-type reaction such as HCl, $H_3PO_4$, $H_2SO_4$, oxalic acid, maleic acid, maleic anhydride and organic sulfonic acids (e.g. P-toluene sulfonic acid). The most preferred acid catalyst is HCl. The preferred ratio of total solids to water is preferably about 0.05 grams to about 0.5 grams total solids per milliliter of solvent.

The intended product may be recovered from the reaction mixture by first cooling to room temperature or less, then diluting the reaction mixture with more solvent (i.e. water) and then isolating the solid product by filtration. This crude product may be washed with water and directly dried or, alternatively, after isolation it may be redissolved in acetone and filtered before solvent evaporation.

The preferred trihydroxybenzophenone compounds are made by the reaction of 2,3,4-trihydroxybenzophenone with trihydroxybenzene [see formula (II)]; with 4-chlororesorcinol [see formula (III)]; and 3-methoxy-5-hydroxyphenol [see formula (IV)].

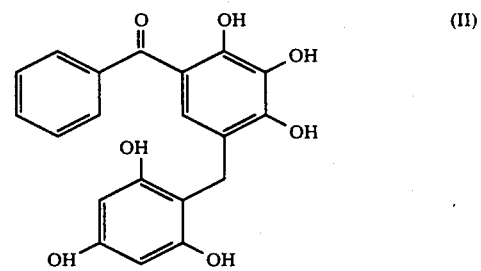
(II)

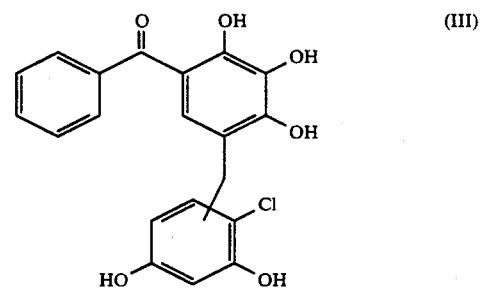
(III)

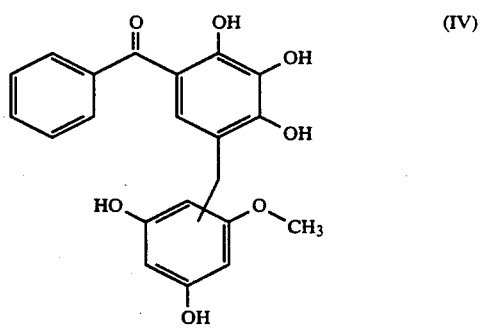
(IV)

The trihydroxybenzophenone compounds of this invention may be converted into the photoactive compounds (PAC's) of formula (V) by their condensation with o-naphthoquinone diazide sulfonyl compounds. Any o-naphthoquinone diazide sulfonyl compound used in making photoresist sensitizers may be employed herein. The most preferred o-naphthoquinone diazide sulfonyl ester moieties are derived from 3-diazo-3,4-dihydro-4-oxo-naphthalene-1-sulfonic acid chloride (also known as 1,2-naphthoquinone-(2)-diazo-4-sulfonic acid chloride or Diazo M) or 6-diazo-5,6-dihydro-5-oxo-naphthalene-1-sulfonic acid chloride (also known as 1,2-napthaquinone-(2)-diazo-5-sulfonic acid chloride or Diazo L). These 4- and 5-ester groups or moieties respectively have the following chemical formulae (IX) and (X):

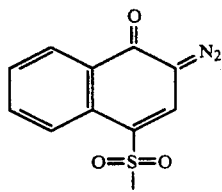

(IX)

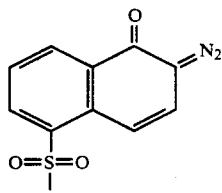

(X)

It is understood that the present invention covers the use of o-naphthoquinone diazide sulfonyl moieties singly or in mixtures in the condensation reaction with these trihydroxybenzophenone compounds. Also, the present invention encompasses separate reactions of these trihydrozybenzophenon compounds with different o-naphthoquinone diazide sulfonyl moieties followed by blending those reaction products together.

This condensation reaction may be carried under any conventional ester condensation conditions. Preferably, these ester compounds of formula (V), above, are prepared by first dissolving the sulfonic acid halide precursor, preferably, the sulfonic acid chloride, in a suitable solvent. Suitable solvents include acetone, dioxane, gamma-butyrolactone, methylene chloride, tetrahydrofurfural alcohol and the like. The trihydroxybenzophenone compounds of formula (I) is then added to this solution. It is advantageous to carry out this reaction in the presence of an acid-scavenging base, such as alkali metal carbonates or bicarbonates, alkaline earth metal carbonates or bicarbonates, tertiary aliphatic amines or pyridine or pyridine derivatives.

The esterification products of this reaction may be recovered from the reaction mixture by any conventional means, preferably by precipitation into acidified water, followed by filtration and drying.

The preferred photoactive compounds (sometimes known as "sensitizers") are those made from the preferred trihydroxybenzophenone compound precursors listed above, namely, 2,3,4-trihydroxy-5-methylolbenzophenone with trihydroxybenzene [see formula (VI)]; with 4-chloro-resorcinol [see formula (VII)]; and with 3-methoxy-5-hydroxyphenol [see formula (VIII)], all of which are as follows:

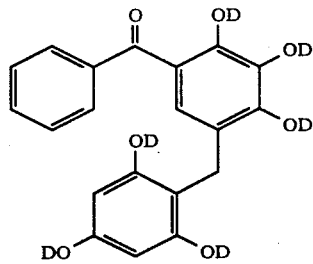

(VI)

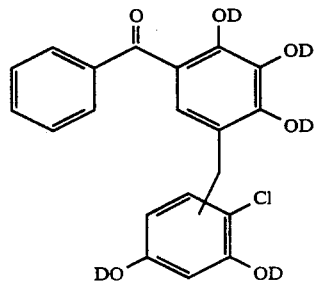

(VIII)

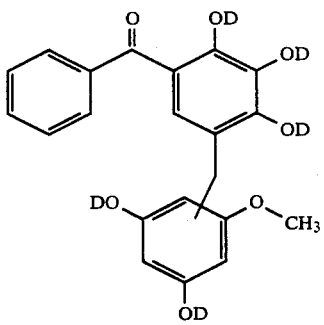

(VIII)

In these photoactive compounds, the D is most preferably 3-diazo-3,4-dihydro-4-oxo-naphthalene-1-sulfonyl; 6-diazo-5,6-dihydro-5-oxo-naphthalene-1-sulfonyl or hydrogen with the proviso that at least four of the D's are one or both of said sulfonyl moieties.

At least one of the ester compounds of the present invention may be mixed with an alkali-soluble resin or resins to make radiation sensitive mixtures which are useful as positive-working photoresist compositions. The term "alkali-soluble resin" is used herein to mean a resin which will dissolve completely in an aqueous alkaline developing solution conventionally used with positive-working photoresist compositions. Suitable alkali-soluble resins include phenol-formaldehyde novolak resins, cresol-formaldehyde novolak resins, and polyvinyl phenol resins, preferably having a molecular weight of about 500 to about 40,000, and more preferably from about 800 to 20,000. These novolak resins are preferably prepared by the condensation reaction of phenol or cresols with formaldehyde and are characterized by being light-stable, water-insoluble, alkali-soluble and film-forming. The most preferred class of novolak resins is formed by the condensation reaction between a mixture of meta- and para-cresols with formaldehyde having a molecular weight of about 1,000 to about 10,000. The preparation of examples of such suitable resins is disclosed in U.S. Pat. Nos. 4,377,631; 4,529,682; and 4,587,196, all which issued to Medhat Toukhy and are incorporated herein by references in their entireties.

Other photoactive compounds may also be added to the radiation sensitive mixtures of the present invention. These other photoactive compounds may include o-quinonediazide esters derived from polyhydric phenols, alkyl-polyhydroxyphenones, aryl-polyhydroxyphenones, and the like which can contain up to six or more sites for esterification. The most preferred o-quinonediazide esters are derived from 3-diazo-3,4-dihydro-4-oxo-naphthalene-1-sulfonic acid chloride and 6-diazo-5,6-dihydro-5-oxo-naphthalene-1-sulfonic acid chloride When other photoactive compounds are used in radiation sensitive mixtures besides the photoactive compounds of the present invention, the amount of photoactive compounds of the present invention should be at least about 5% by weight, preferably 10–100% by weight of the total photoactive compounds present.

The proportion of the photoactive compound in the radiation sensitive mixture may preferably range from about 5 to about 30%, more preferably from about 8 to about 20% by weight of the non-volatile (e.g. non-solvent) content of the radiation sensitive mixture. The proportion of total binder resin of this present invention in the radiation sensitive mixture may preferably range from about 70 to about 95%, more preferably, from about 80 to 92% of the non-volatile (e.g. excluding solvents) solids content of the radiation sensitive mixture.

These radiation sensitive mixtures may also contain conventional photoresist composition ingredients such as solvents, actinic and contrast dyes, anti-striation agents, plasticizers, speed enhancers, and the like. These additional ingredients may be added to the binder resin and photoactive compound before the solution is coated onto the substrate.

The resins and sensitizers may be dissolved in a solvent or solvents to facilitate their application to the substrate. Examples of suitable solvents include methoxyacetoxy propane, ethyl cellosolve acetate, n-butyl acetate, ethyl lactate, ethyl 3-ethoxy propionate, propylene glycol alkyl ether acetates, or mixtures thereof and the like. Cosolvents such as xylene or n-butylacetate may also be used. The preferred amount of solvent may be from about 50% to about 500%, or higher, by weight, more preferably, from about 100% to about 400% by weight, based on combined resin and sensitizer weight.

Actinic dyes help provide increased resolution on highly reflective surfaces by inhibiting back scattering of light off the substrate. This back scattering causes the undesirable effect of optical notching, especially on a highly reflective substrate topography. Examples of actinic dyes include those that absorb light energy at approximately 400–460 nm [e.g. Fat Brown B (C.I. No. 12010); Fat Brown RR (C.I. No. 11285); 2-hydroxy-1,4-naphthoquinone (C.I. No. 75480) and Quinoline yellow A (C.I. No. 47000)] and those that absorb light energy at approximately 300-340 nm [e.g. 2,5-diphenyloxazole (ppO-Chem. Abs. Reg. No. 92-71-7) and 2-(4-biphenyl)-6-phenyl-benzoxazole (pBBO-Chem. Abs. Reg. No. 17064-47-0)]. The amount of actinic dyes may be up to ten percent weight levels, based on the combined weight of resin and sensitizer.

Contrast dyes enhance the visibility of the developed images and facilitate pattern alignment during manufacturing. Examples of contrast dye additives that may be used together with the radiation sensitive mixtures of the present invention include Solvent Red 24 (C.I. No. 26105), Basic Fuchsin (C.I. 42514), Oil Blue N (C.I. No. 61555) and Calco Red A (C.I. No. 26125) up to 10% weight levels, based on the combined weight of resin and sensitizer.

Anti-striation agents level out the photoresist coating or film to a uniform thickness. Anti-striation agents may be used up to five percent weight levels, based on the combined weight of resin and sensitizer. One suitable class of anti-striation agents is non-ionic silicon-modified polymers. Non-ionic surfactants may also be used for this purpose, including, for example, nonylphenoxy poly(ethyleneoxy) ethanol; octylphenoxy (ethyleneoxy) ethanol; and dinonyl phenoxy poly(ethyleneoxy) ethanol.

Plasticizers improve the coating and adhesion properties of the photoresist composition and better allow for the application of a thin coating or film of photoresist which is smooth and of uniform thickness onto the substrate. Plasticizers which may be used include, for example, phosphoric acid tri-(B-chloroethyl)-ester; stearic acid; dicamphor; polypropylene; acetal resins; phenoxy resins; and alkyl resins up to ten percent weight levels, based on the combined weight of resin and sensitizer.

Speed enhancers tend to increase the solubility of the photoresist coating in both the exposed and unexposed areas, and thus, they are used in applications where speed of development is the overriding consideration even though some degree of contrast may be sacrificed, i.e., in positive resists while the exposed areas of the photoresist coating will be dissolved more quickly by the developer, the speed enhancers will also cause a larger loss of photoresist coating from the unexposed areas. Speed enhancers that may be used include, for example, picric acid, nicotinic acid or nitrocinnamic acid at weight levels of up to 20%, based on the combined weight of resin and sensitizer.

The prepared radiation sensitive resist mixture, can be applied to a substrate by any conventional method used in the photoresist art, including dipping, spraying, whirling and spin coating. When spin coating, for example, the resist mixture can be adjusted as to the percentage of solids content in order to provide a coating of the desired thickness given the type of spinning equipment and spin speed utilized and the amount of time allowed for the spinning process. Suitable substrates include silicon, aluminum or polymeric resins, silicon dioxide, doped silicon dioxide, silicon resins, gallium arsenide, silicon nitride, tantalum, copper, polysilicon, ceramics and aluminum/copper mixtures. The coating surfaces of these substrates may or may not be primed with a conventional adhesion promoter (e.g. hexamethyldisilazane) before the photoresist coating is applied.

The photoresist coatings produced by the above described procedure are particularly suitable for application to silicon wafers coated with a silicon dioxide or silicon nitride layer such as are utilized in the production of microprocessors and other miniaturized integrated circuit components. An aluminum or aluminum-coated substrates may be used as well. The substrate may also comprise various polymeric resins especially transparent polymers such as polyesters and polyolefins.

After the resist solution is coated onto the substrate, the coated substrate is baked at approximately 70° C. to 125° C. until substantially all the solvent has evaporated and only a uniform radiation sensitive coating remains on the substrate.

The coated substrate can then be exposed to radiation, especially ultraviolet radiation, in any desired exposure pattern, produced by use of suitable masks, negatives, stencils, templates, and the like. Conventional imaging process or apparatus currently used in processing photoresist-coated substrates may be employed with the present invention. While ultraviolet (UV) light is the preferred source of radiation, other sources of radiation such as visible light, electron or ion beam and X-ray radiant energy may be used instead.

The exposed resist-coated substrates are preferably subjected to a post exposure bake at a temperature from about 100° C. to about 130° C. from about 30–300 seconds to enhance image quality and resolution.

The exposed resist-coated substrates are next developed in an aqueous alkaline developing solution. This solution is preferably agitated, for example, by nitrogen gas agitation. Examples of aqueous alkaline developers include aqueous solutions of tetramethylammonium hydroxide, sodium hydroxide, potassium hydroxide, ethanolamine, choline, sodium phosphates, sodium carbonate, sodium metasilicate, and the like. The preferred developers for this invention are aqueous solutions of either alkali metal hydroxides, phosphates or silicates, or mixtures thereof, or tetramethylammonium hydroxide.

Alternative development techniques such as spray development or puddle development, or combinations thereof, may also be used.

The substrates are allowed to remain in the developer until all of the resist coating has dissolved from the exposed areas. Normally, development times from about 10 seconds to about 3 minutes are employed.

After selective dissolution of the coated wafers in the developing solution, they are preferably subjected to a deionized water rinse to fully remove the developer or any remaining undesired portions of the coating and to stop further development. This rinsing operation (which is part of the development process) may be followed by blow drying with filtered air to remove excess water. A post-development heat treatment or bake may then be employed to increase the coating's adhesion and chemical resistance to etching solutions and other substances. The post-development heat treatment can comprise the baking of the coating and substrate below the coating's thermal deformation temperature.

In industrial applications, particularly in the manufacture of microcircuitry units on silicon/silicon dioxide-type substrates, the developed substrates may then be treated with a buffered hydrofluoric acid etching solution or plasma gas etch. The resist compositions of the present invention are believed to be resistant to a wide variety of acid etching solutions or plasma gases and provide effective protection for the resist-coated areas of the substrate.

Later, the remaining areas of the photoresist coating may be removed from the etched substrate surface by conventional photoresist stripping operations.

The present invention is further described in detail by means of the following Examples. All parts and percentages are by weight unless explicitly stated otherwise.

EXAMPLE 1

Synthesis of 5-Methylol-2,3,4-Trihydroxybenzophenone emoloying 2.5 Hours Reaction Time at 40°–47° C.

2,3,4-Trihydroxybenzophenone [300 gm (1.2 moles)] was added to a 3 liter, three neck flask equipped with mechanical agitation, a thermometer, a condenser, and an addition funnel. An aqueous solution of sodium hydroxide [208 gm 98% by weight NaOH dissolved in 1 liter of distilled water (5.1 moles NaOH)] was added slowly to the flask. A dark aqueous solution of the trihydroxybenzophenone was formed rapidly. A slight exotherm was observed causing the solution temperature to rise to approximately 48° C.

An aqueous formaldehyde solution (36.5% by weight) [123.3 gm (1.5 moles)] was then added dropwise through the addition funnel at a controlled rate so not to cause the reaction temperature to exceed 50° C. Half the formaldehyde solution was added rapidly in five minutes, and the second half over a total of 80 minutes. After addition, the reaction was allowed to proceed for an additional 80 minutes before it was acidified with a dilute 37% aqueous hydrochloric acid solution by weight [513 gm (5.2 moles HCl)]. The change in the pH of the solution to a neutral or slightly acidic was associated with a change in its color to a yellowish orange.

The reaction solution was transferred to a larger container filled with 3 liters of distilled water under vigorous agitation. The reaction solution was dripped slowly into the agitated water over 30 minutes duration. A light, solid precipitate was formed. The solid product was filtered out and dried in a vacuum oven at 50° C. for about 20 hours to remove substantially all water in the product.

The dried product weighted 306.5 gm which represented a 90.7% yield based on a theoretical yield of 38 gm.

The structure of the above titled compound was confirmed by infrared spectral analysis and by proton NMR. The observed NMR ratio of the aliphatic hydrogens to the aromatic hydrogens was 0.296. Compared with the theoretical ratio value of 0.33 for this compound, the product purity is 89.7% by moles. High pressure liquid chromatography detected the presence of approximately 7% by weight of trihydroxybenzophenone starting material indicated that this was the major impurity.

EXAMPLE 2

Synthesis of the Adduct of 1,3,5-Trihydroxybenzene With 2,3,4-Trihydroxybenzophenone-5-Methylol 1,3,5-trihydroxybenzene [126 gm (1 mole)] was dissolved in 770 ml of distilled water under agitation in a one liter flask. This solution was acidified with 4 ml hydrochloric acid (37%). 2,3,4-trihydroxybenzophenone-5-methylol [26 gm (0.1 moles)] was added to the reaction mixture and heated gradually up to 80° C. The reaction was allowed to continue for 18 hours before it was cooled to room temperature. The reaction solution was treated with an additional 500 ml of distilled water to precipitate the product out of solution. The product was filtered out and washed repeatedly with distilled water. The purity of the product was checked by means of thin layer chromatography to give one spot. Then it was dried in a vacuum oven at 50° C. for 20 hours. The yield of this reaction was 87% [32 gm].

EXAMPLE 3

Synthesis of The Adduct of 4-Chlororesorcinol With 2,3,4-Trihydroxybenzophenone-5-Methylol 4-Chlororesorcinol [144.5 gm (1 mole)] was dissolved in 1,200 ml of distilled water under agitation in a one liter flask. This solution was acidified with 4 ml hydrochloric acid (37%). 2,3,4-Trihydroxybenzophenone-5-methylol [26 gm (0.1 moles)] was added to the reaction mixture and heated gradually up to 80° C. The reaction was allowed to continue for 72 hours before it was cooled to room temperature. The reaction solution was treated with an additional 500 ml of distilled water to precipitate the produCt Out of solution. The product was filtered out and washed repeatedly with distilled water. The purity of the product was checked by means of thin layer chromatography to give one spot. Then it was dried in a vacuum oven at 50° C. for 20 hours. The yield of this reaction was 71% [27.4 gm].

EXAMPLE 4

Synthesis of The Adduct of 1,3-Dihydroxy-5-Methoxybenzene with 2,3,4-Trihydroxybenzophenone-5-Methylol 1,3-Dihydroxy-5-methoxybenzene [10 gm (0.071 mole)] was dissolved in 200 ml of distilled water under agitation in a one liter flask. This solution was acidified with 2 ml hydrochloric acid (37%). 2,3,4-Trihydroxybenzophenone-5-methylol [3 gm (0.0115 moles)] was added to the reaction mixture and heated gradually up to 80° C. The reaction was allowed to continue for 18 hours before it was cooled to room temperature. The reaction solution was treated with an additional 200 ml of distilled water to precipitate the product out of solution. The product was filtered out and washed repeatedly with distilled water. The purity of the product was checked by means of thin layer chromatography to give one spot. Then it was dried in a vacuum oven at 50° C. for 20 hours. The yield of this reaction was 91% [4 gm].

EXAMPLE 5

Esterification of the Adduct of Example 3 with 5 Moles of 3-Diazo-3,4-Dihydro-4-Oxo-naphthalene-1-Sulfonic Acid Chloride The esterification was performed in a 600 mL beaker wrapped in aluminum foil and fitted with a mechanical stirrer and a pH probe. The adduct of Example 3 and 3-diazo-3,4-dihydro-4-oxo-naphthalene-1-sulfonic acid chloride [7.9 gm, 0.0665 mole), dioxane [250 mL] and water [20 mL] were added to the beaker and the mixture was stirred until all the solids had dissolved. To the solution was added triethylamine [7 gm] at such a rate as to maintain the pH of the solution at 7.0-7.8. After stirring at room temperature 3.75 hours after beginning addition, the reaction mixture was acidified to pH 2.5 with 32% HCl and drowned into water [700 mL] containing HCl [6 gm of 32% solution]. The resulting red precipitate was isolated by filtration and washed with deionized water [2L].

The solid was collected and dried under vacuum at 40°-45° C. to yield a solid [18 gm, 57% yield].

The liquid chromatogram of the titled substance was recorded using a 4.5 ID×250 mm ECC8 column with 65% acetonitrile and 35% high ionic strength buffer at a flow rate of 2.5 mL/min. The following major peaks eluted and are reported as retention time and (area percent); 1.2 min. (5%); 1.2 min. (2.6%); 1.47 min. (4.4%); 1.9 min. (10.3%); 4.17 min. (3.5%); 5.07 min. (62.1%).

The high ionic strength buffer is made from trifluoroacetic acid anhydride [1.5 mL], tetramethylammonium hydroxide pentahydrate [1.8 gm], and water [lL]. The pH of this solution is adjusted to 3.0±0.1 using sodium hydroxide [0.1N].

Additionally, the 2 gm sample of the titled compound was dissolved in methylene chloride and was twice passed over 16 gm of Grade IV neutral alumina held in ethyl acetate on a short chromatography column. The product was isolated by low temperature evaporation, about 40° C., using a rotary evaporator and weighed 0.6 gm.

The liquid chromatogram of the above substance was obtained in the same manner as the titled substance and exhibited the following major peaks expressed as retention time in minutes and (area percent): 0.86 min. (2.8%); 1.9 min. (3.5%); 5.1 min. (74.9%).

EXAMPLE 6

Esterification of the Adduct of Examole 2 with 6 Moles of 3-Diazo-3,4-Dihvdro-4-Oxo-naohthalene-1-Sulfonic Acid Chloride The reaction was performed on a 600 mL beaker which had been wrapped with aluminum foil and was fitted with a mechanical stirring apparatus and a pH probe. To the flask was added the adduct of Example 2 and 3-diazo-3,4-dihydro-4-oxo-naphthalene-1-sulfonic acid chloride 6.62 gm, 0.0246 moles], p-dioxane [100 mL], and deionized water [10 mL]. The mixture was stirred until all the solids were dissolved. Triethylamine [3.49 gm] was added to the solution over 15 minutes. The reaction mixture was allowed to stir for 70 minutes after the end of addition, and it was acidified with HCl [1.6 gm of 32% solution]. The solution was poured slowly into deionized water [1,500 mL] containing HCl [13 gm of 32% solution] and allowed to stand 16 hours. The mixture was filtered and washed with deionized water. It was dried at 40°-45° C. to yield 3.6 gm of product.

The ester product was suspended in methylene chloride [15 gm] and the solution was decanted and passed down a chromatography column containing neutral alumina [38 gm, Grade III] in ethyl acetate. A solid was isolated by low temperature, about 40° C., evaporation of the ethyl acetate in a rotary evaporator and combined with the dried residue of the initial suspension, total weight 2.8 gm.

EXAMPLE 7

Resist Formulation

A resist formulation prepared with photoactive compound, based on the product of Example 5, was evaluated. The resist was prepared by dissolving 24.5 gm of a mixture of 3.06 gm of the product of Example 5 and 21.44 gm of a cresol novolak resin in 75.5 gm of a solvent consisting of 85% ethylcellosolve acetate, 7.5% butyl acetate and 7.5% xylene. The novolak resin used in this formulation was prepared from a cresol mixture of 60% m-cresol and 40% p-cresol and formaldehyde. This resin is very soluble in aqueous alkaline developers. A one micron thick coating of this resin dissolves completely in the developer used in this test in 3-5 seconds.

The resist solution was microfiltered through 0.2 μm filter and applied to the silicon wafer. A dry coating thickness of about one micron of the resist was formed uniformly on the wafer by spin coating and drying in an air convection oven for 30 minutes at 100° C. The coating was exposed to patterned UV radiation using Ultratech 1000 step and repeat unit (0.30 NA lens). The resist was then developed in immersion for 50 seconds in HPRD-419 developer produced by Olin Hunt Specialty products at room temperature. Resist patterns of high definition were resolved at a photospeed of about 150–160 mJ/Cm². Small geometries of 0.9 μm lines and spaces were cleanly developed. Vertical to concaved resist wall profiles were observed by scanning electron microscopic examination of this resist.

COMPARATIVE EXAMPLE 1

A resist formulation prepared according to Example 7 but replacing the photoactive compound with a trihydroxybenzophenone/naphthoquinone diazide ester commonly used in the industry was evaluated. This conventional photoactive compound was prepared by condensing 2 moles of 1,2-naphthoquinone-5-sulfonyl chloride with 1 mole of 2,3,4-trihydroxybenzophenone. This resist was evaluated in a similar process as shown in Example 7. The resist film was completely dissolved off the water during the development. No image remained on the wafer.

The photoactive compound of Example 5 provided much higher naphthoquinonediazide functionality (up to 6) and dissolution inhibition than this conventional photoactive compound based on trihydroxybenzophenone (up to 3).

This was demonstrated in comparing Example 7 with comparative Example 1. In both examples, the novolak used is highly alkaline soluble and requires a highly inhibitor sensitizer to provide a resist with sufficient contrast between exposed and unexposed resist area. In addition, the amount of the photoactive compound used in both examples was 12.5% by weight in the resist films. At this concentration, the photoactive compound of Example 5 of the invention was sufficiently inhibiting the novolak from dissolving in the unexposed areas, while in comparative Example 1 it was not. A particular advantage for using a highly inhibiting photoactive compound is in the area of resist film transparency. The ability to use low concentrations of the photoactive compound with good development contrast provides increased resist film transparency. Consequently, the ability of the resist to bleach and produce cleanly developed smaller features increases. This improves the resolution and the steepness of the resist image.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A trihydroxybenzophenone compound of the formula (I):

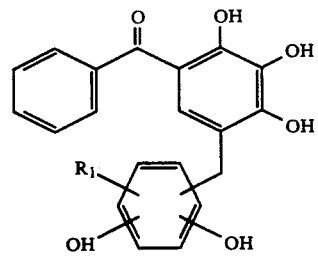

where $R_1$ is selected from the group consisting of hydroxyl group, halide group, a lower alkyl group having 1 to 4 carbon atoms, and a lower alkoxy group having 1 to 4 carbon atoms.

2. The trihydroxybenzophenone compound of claim 1 having formula (II):

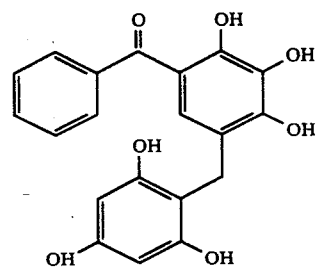

3. The trihydroxybenzophenone compounds of claim 1 having the formula (III):

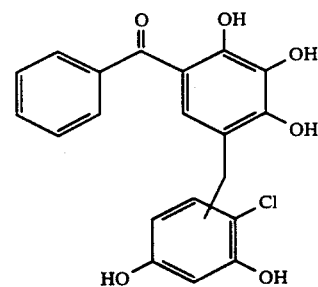

4. The trihydroxybenzophenone compounds of claim 1 having the formula (IV):

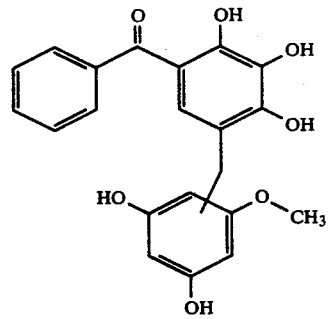

5. The trihydroxybenzophenone compound of claim 1 wherein $R_1$ is selected from the group consisting of a hydroxy group, a chloro group, and a methoxy group.

* * * * *